United States Patent [19]
Garrett

[11] 3,942,510
[45] Mar. 9, 1976

[54] HEATING DEVICE

[75] Inventor: William Garrett, New York, N.Y.

[73] Assignee: General Kinetronics, New York, N.Y.

[22] Filed: Aug. 21, 1974

[21] Appl. No.: 499,329

[52] U.S. Cl. .............................................. 126/263
[51] Int. Cl.² .......................... F24J 1/00; F24J 3/04
[58] Field of Search ................... 126/246, 261–263, 126/265–269

[56] References Cited
UNITED STATES PATENTS

| | | | |
|---|---|---|---|
| 261,762 | 7/1882 | Quick | 126/262 |
| 865,940 | 9/1907 | Randolph | 126/263 |
| 947,062 | 1/1910 | Hawkins | 126/261 |
| 1,016,791 | 2/1912 | Smith | 126/261 |
| 1,174,404 | 2/1916 | Szotak | 126/263 |
| 1,774,505 | 9/1930 | Deppeler | 126/263 |
| 3,287,140 | 11/1966 | Brussell | 126/262 |
| 3,685,507 | 8/1972 | Donnelly | 126/263 |

*Primary Examiner*—William E. Wayner
*Assistant Examiner*—Ronald C. Capossela
*Attorney, Agent, or Firm*—Kane, Dalsimer, Kane, Sullivan and Kurucz

[57] ABSTRACT

The disclosure is of a unitary, self-contained apparatus for flameless heating. The device comprises a tubular container divided into heat-generating and heat utilizing zones. The source of heat employed is the exothermia of a chemical reaction, particularly of chemical reactions initiated by the presence of water. The device of the invention is, because of its particular and novel construction, especially useful for those applications requiring high caloric yields for prolonged periods of time.

14 Claims, 5 Drawing Figures

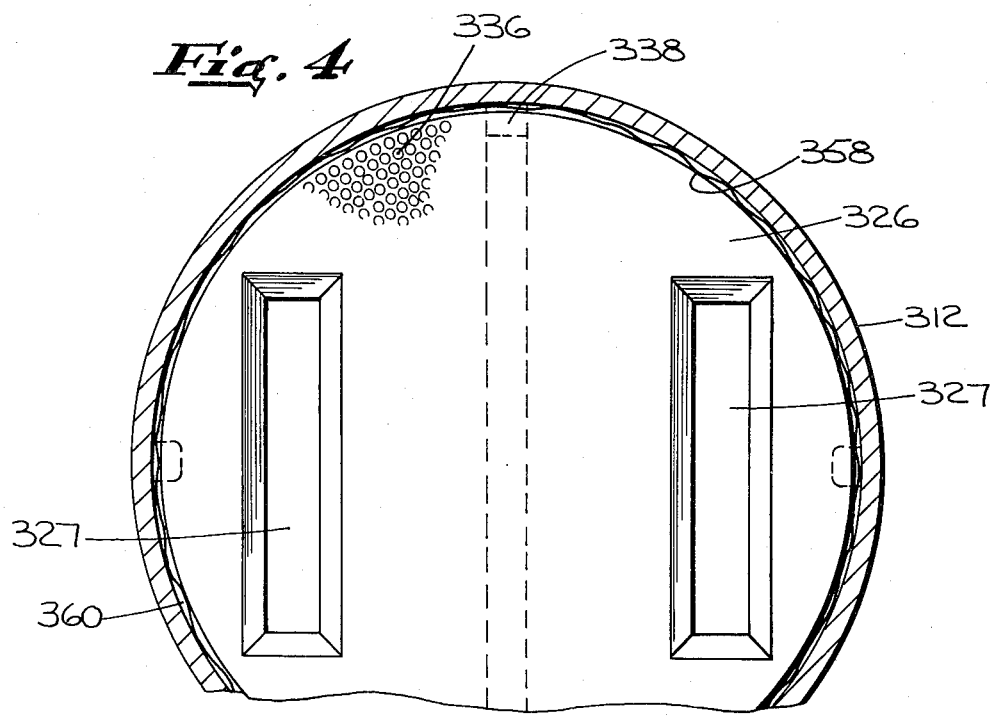
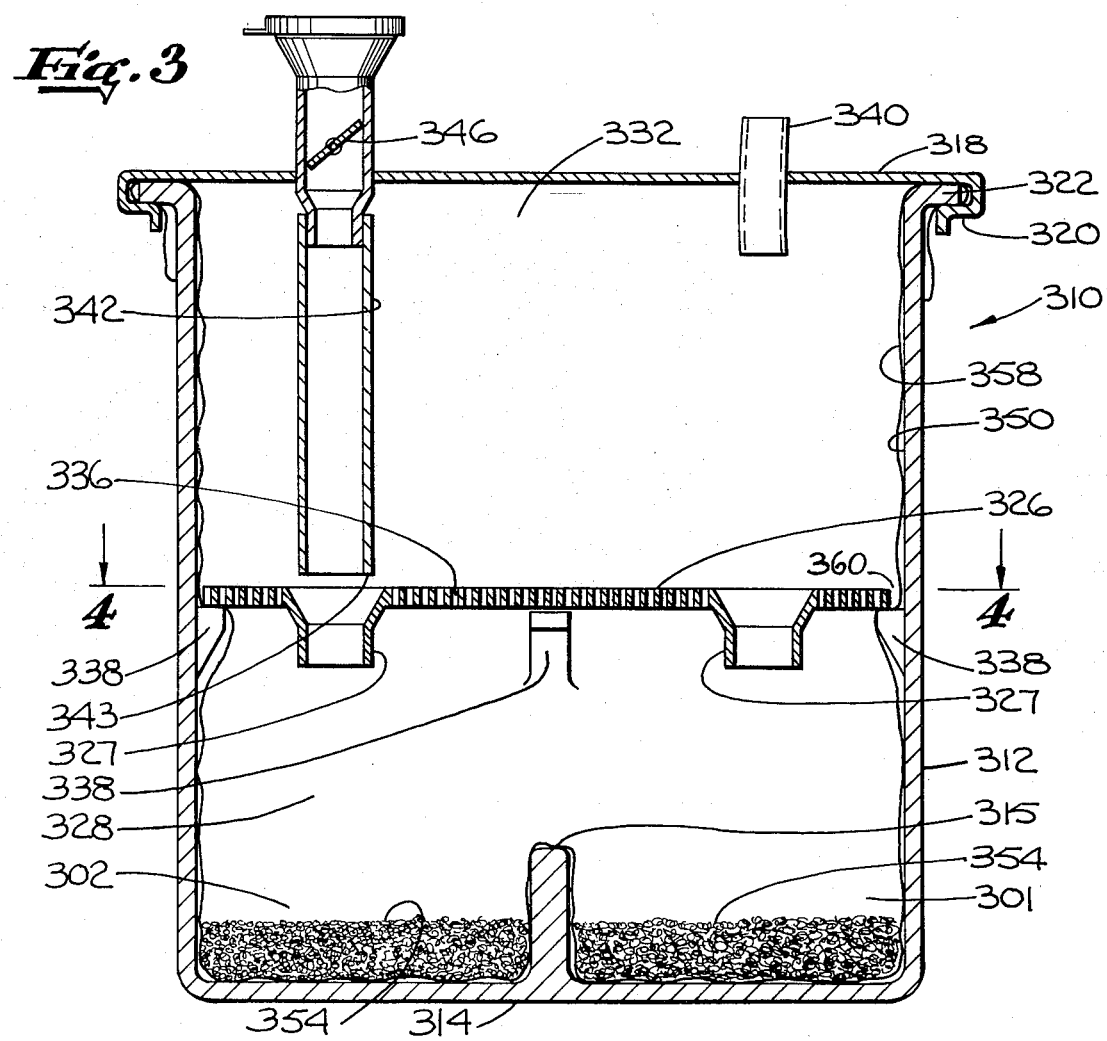

3,942,510

HEATING DEVICE

BACKGROUND OF THE INVENTION

1. Field of the Invention

The invention is concerned with portable heat-generating devices and more particularly concerns heating devices which employ and utilize heat generated by the exothermia of a flameless chemical reaction.

2. Brief Description of the Prior Art

Prior to my invention, apparatus and devices comprising heaters employing chemical reactions as the heating means were known. In general, the devices of the prior art have not enjoyed a widespread commercial use because they are too complex in construction or are too inefficient for practical use. The device of my invention provides useable heat in quantity and for periods of time sufficient even for the sterilization of utensils, to cook meats, carry out chemical reactions and like uses where high caloric yields are required for prolonged periods of time.

SUMMARY OF THE INVENTION

The invention comprises a unitary, self-contained apparatus for flameless heating which comprises; a tubular container having at least one opening; closures for the openings; a chamber defined by said tubular container with closures; means for dividing the chamber into a heat-generating zone and a heatutilizing zone, said means being pervious to heat and gases; means for venting said heat-utilizing zone to the exterior of said container; and a conduit communicating between said chamber and the exterior of the closed container.

The apparatus of the invention is useful for warming and cooking foods; sterilizing utensils, liquids and medical instruments; providing medicinal vapors; and like applications where the use of flaming fuels or electricity is undesirable or unavailable for the generation of heat.

BRIEF DESCRIPTION OF THE DRAWINGS

FIG. 3 is a cross-sectional side elevation of an alternate embodiment of the invention.

FIG. 4 is a cross-sectional view along lines 4—4 of FIG. 3.

DETAILED DESCRIPTION OF THE INVENTION

The invention may be conveniently described by referring to those embodiments of the invention shown in the accompanying drawings of FIGS. 1–5, inclusive.

Figure 1:
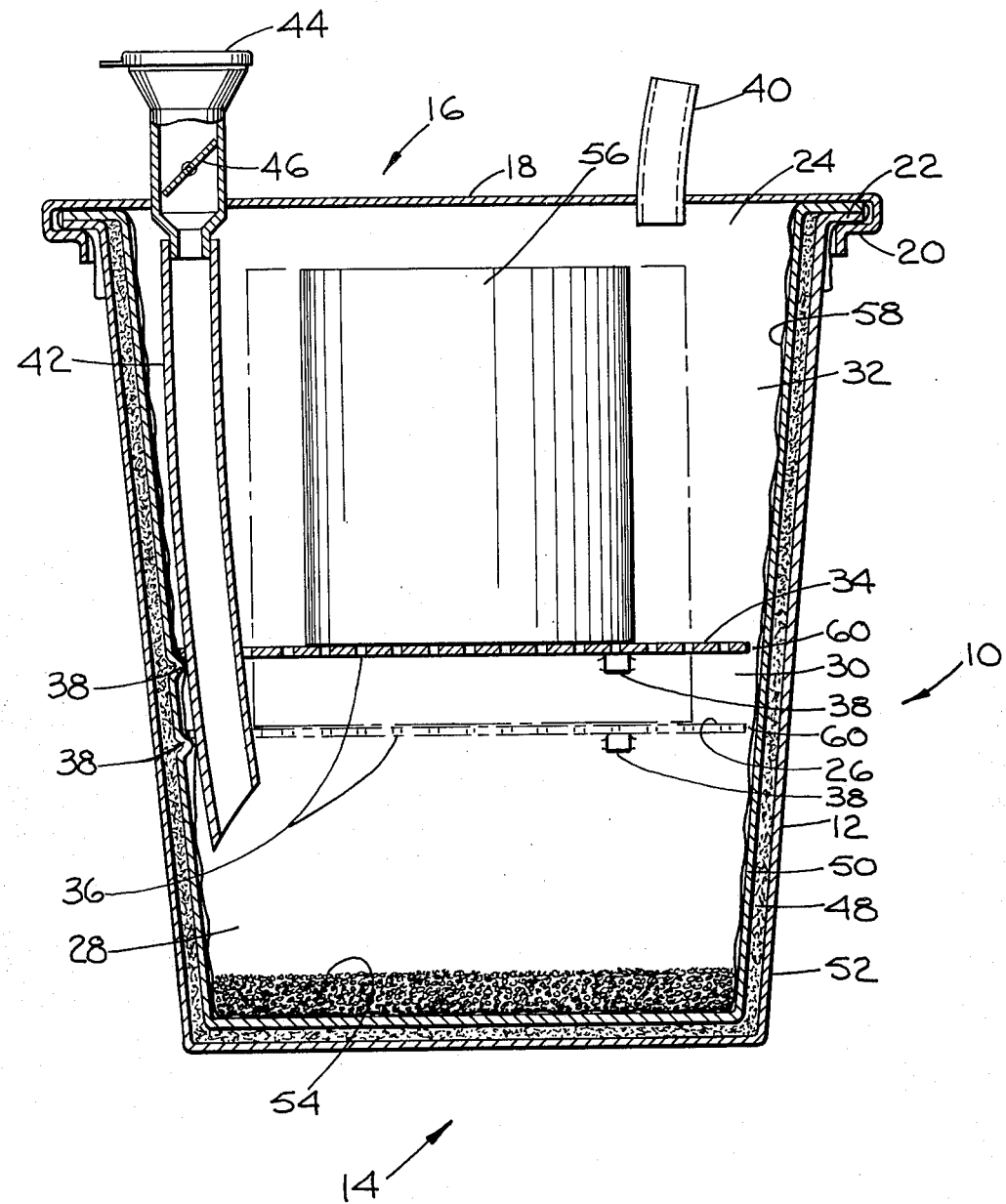
FIG. 1 is a cross-sectional side elevation of an embodiment of the invention.

FIG. 1 is a cross-sectional side elevation of an embodiment of the invention referred to generally by the numeral 10. Device 10 is a tubular container having side walls 12 integral with closed end 14 and an open end 16. The open end 16 is fitted with a closure 18 which seals the end 16 by a snap-fit 20 which cooperates with flange 22 disposed radially about the outer periphery of side-wall 12. The closed device 10 defines a chamber 24 which is divided by a separator 26 into a heat-generating zone 28 and a heat-utilizing zone 30.

Optionally, other heat-utilizing zones or heat-generating zones such as zone 32 may be defined by the introduction of additional separators such as separator 34. Separators 26, 34 are pervious to heat and gases such as by means of perforations 36. These perforations are preferably of a size permitting the passage of steam under pressure, but insufficient to permit the ready passage of water. The precise and optimal diameter of the perforations will vary depending on the nature of the material employed to fabricate the separators 26, 34. For example, a hydrophobic polymeric material may have larger diameter perforations than are advantageously used in hydrophyllic materials. The optimal diameter of the perforations may be determined by trial and error. Separators 26, 34 are shown as removeable, resting on inwardly directed projections 38 of wall 12. Obviously, when a single separator is employed, it may be affixed permanently within chamber 24, provided there is a means of access to zone 28 from outside the device 10. The heat-utilizing zone 32 is vented to the exterior by vent 40 so that excess pressures during operation do not build up within device 10. In addition, tubular conduit 42 passes through apertures in separators 26, 34 to provide communication between heat-generating zone 28 and the exterior of device 10. Advantageously, the end of conduit 42 proximal to the exterior is formed in the shape of a funnel 44 and has a means of closure, shown here as a butterfly valve 46.

Advantageously, the device 10 is constructed of materials having a low thermal conductivity (K factor) coupled with structural strength. Illustratively, the side-walls 12 and closure 18 may be fabricated from non-cellular synthetic polymeric materials having a low K factor such as low density polyethylene, polyurethane, polystyrene, polyurea, polyamide, polypropylene, polycarbonate, acrylonitrile-butadiene-styrene copolymer and like polymerics; rigid cellular polymeric foams such as foamed polyethylene, polypropylene, polyurethane, ureaformaldehyde, polystyrene and like rigid polymeric foams; composite materials such as laminates of the above described polymeric resins with inorganic materials of low K factor such as fiberglass, perlite, mineral wool, heat reflective metalized fabrics and the like. The most preferred material employed will provide a container wall having a low thermal conductivity, i.e., of less than about 0.5 B.T.U./(hr.) (sq. ft.) (°F/ft.).

As shown in FIG. 1, the side wall 12 has been fabricated from a self-skinning polyurethane foam having a cellular core 48 and outer non-cellular skins 50, 52. Self-skinning polyurethane foams are well known and are particularly advantageous in that they have low K factors, structural strength and may be molded in a single step process; see U.S. Pat. No. 3,824,199.

the device 10 is operated by placing an exothermic heating composition 54 in the heat-generating zone 28 and the material to be heated 56 in the heat-utilizing zone 32. Composition 54 is activated by addition of water and is preferably of the type which releases heat upon oxidation of a metal. Such chemical compositions are well known and need no description herein. Representative of such compositions 54 are those disclosed in U.S. Pat. Nos. 3,079,911 and 3,101,707. With closure 18 in place, a measured amount of water is introduced into zone 28 through conduit 42, activating the exothermic chemical reaction. Generally, a large volume of steam is also generated during the reaction. The heat generated is transmitted through the heat pervious separators 26, 34 to the heat-utilizing zone 32 thereby cooking, sterilizing, etc. the article 56 contained in that zone. Evolved steam passes through the passages 36 and into zone 32 where they bathe the article 56. As shown in the FIG. 1, valve 46 is closed to ensure that all steam vapor passes through zone 32. Excess pressure caused by the evolution of steam is vented through vent 40. Exposure of the article 56 to the steam vapor increases the efficiency of heating, and reduces heating times. The live steam contact also assists sterilization of article 56 when that is desired. It is obvious that article 56 may also be a medicine to be vaporized, in which case the moisturized medicinal vapors are expelled through vent 40 for inhalation by a patient. Upon completion of the exothermic reaction, the article 56 may be removed and the device recharged with fresh composition 54. If it is found that additional heating is required, fresh composition 54 may be charged to the heat-generating zone 28 through conduit 42 along with water for activation, without interruption of the heating cycle. This is an advantage of the device of the invention which provides a means of continued access to the heat-generating compartment, without having to interrupt the heating cycle.

As shown in FIG. 1, a preferred embodiment includes lining the device 10 with a polyethylene or polymeric like film 58. This is a disposable film unit which facilitates cleaning the device 10 after use. Thus after use, the liner 58 may be conveniently removed with expended composition 54 as its contents, and replaced by a fresh liner holding fresh composition. The composition 54 is shown as a loose aggregation. It can also be contained within a porous sachet or like form, however the loose material is advantageously poured through conduit 42 when a second charge is required.

The steam vapors reaching zone 32 are not all vented ultimately to the outside of device 10. A portion of the vapors will condense on the inner wall surface 50 and on the inner surface of closure 18. It is generally undesirable that the water of condensation be dumped on the top surface of the reacting composition 54, since this will tend to cool the top surface. In the device 10 this does not occur, because the passages 36 do not permit the passage of any substantial volume of water, and the pressure of steam passing through further prevents the passage of water in the opposing direction. However, it is desirable for the condensed water to reach the reacting composition 54 to aid in sustaining the reaction. In the preferred device 10 this is accomplished by providing passages 60 between the wall surface 50 and separators 26, 34 which communicate between zones 32 and 28. Water vapor condensing on the surface 50 (or the liner 58 over surface 50) adheres to such surface and is carried by gravity to the bottom of the container where it is absorbed along the edge and bottom of the charge of composition 54. The surface tension of the water droplets adhered to the liner 58 on surface 50 prevents steam pressure along the edges from resisting descent of the water through the relatively large passages 60. This is a particularly advantageous feature, preventing the buildup of condensed water in zone 32 which would tend to cool the article 56 (reducing heating efficiency) and providing for the continuation of the exothermic reaction as disclosed above.

Figure 2:
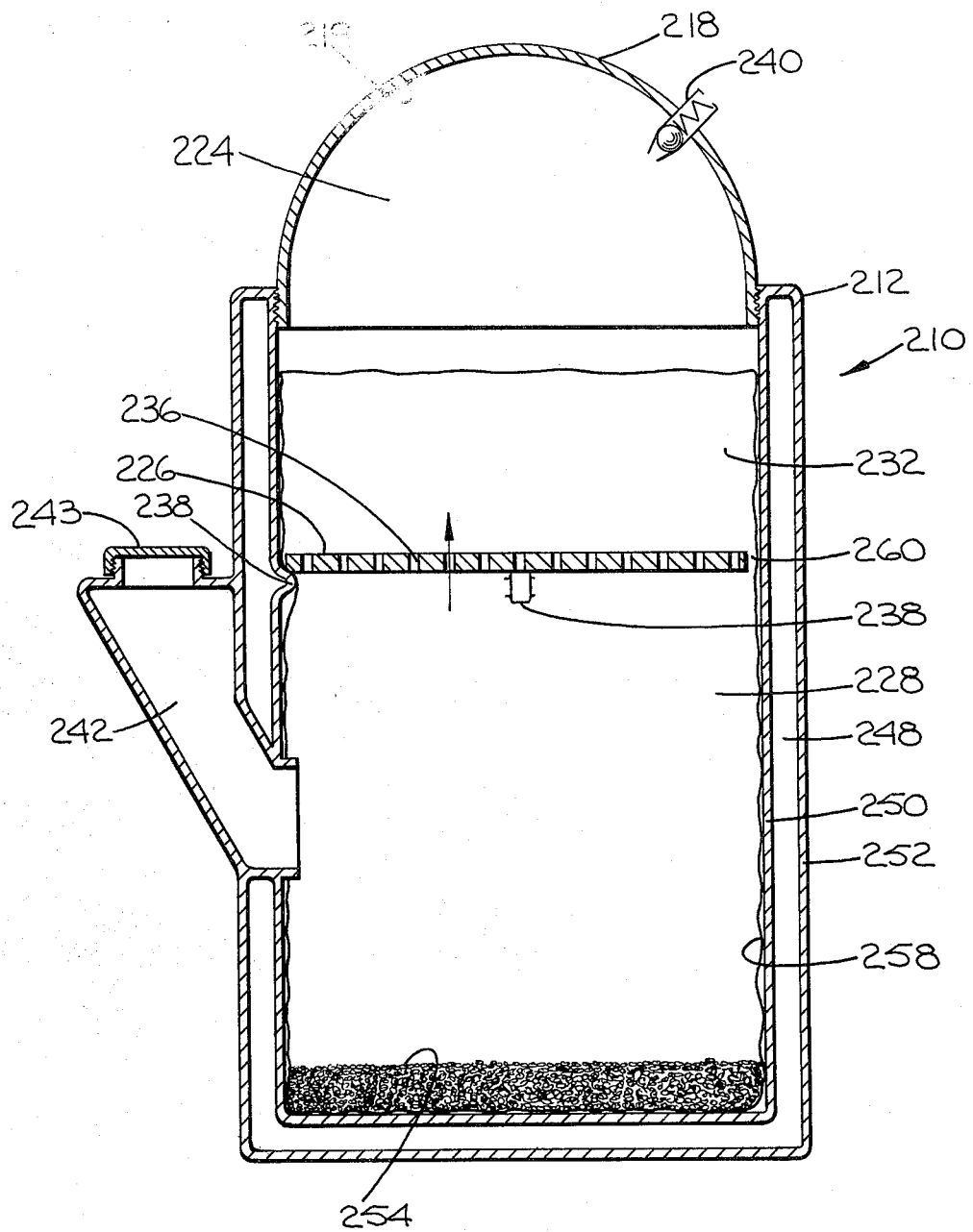
FIG. 2 is a cross-sectional side elevation of a preferred embodiment of the invention.

FIG. 2 is a cross-sectional side elevation of a preferred embodiment of the invention wherein the device 210 comprises a tubular container having a double wall 212 construction with a vacuum chamber 248 between inner wall 250 and outer wall 252. This construction provides a preferred insulating wall 212. The inner chamber 224 is divided into a heat-generating zone 228 and a heat-utilizing zone 232 by heat and gas pervious separator 226 which nests upon projections 238 and which is perforated by apertures 236. The closure 218 of this preferred embodiment has a concave inner surface 219 which facilitates the flow of condensed water vapor, during operation, down the sidewall 250 (shown here lined by disposable plastic bag 258) through passages 260 between separator 226 and wall 250 as described previously in relation to FIG. 1. In the embodiment of FIG. 2, the heat-generating composition 254 may be charged through conduit 242 which passes through sidewall 212 and has a removeable closure 243, shown as a screw-on cap. Water to initiate the exothermic reaction may also be charged through conduit 242. The closure 218 may be removed (in this instance it is shown secured by screw threading to the body of the tubular container) to gain access to the interior of the heat-utilizing chamber 232 and to gain access to the zone 228 by removal of the nested separator 226. The embodiment of FIG. 2 also shows a ball-valve vent 240 which may be designed to vent the chamber 232 when a predetermined steam pressure is exceeded. In this manner, it is possible to carry out a "pressure cooking" procedure or to sterilize under steam pressure, thereby reducing the time required for sterilization of, for example, surgical instruments. The embodiment of FIG. 2 is operated in the same manner as device 10 described in FIG. 1, and is a preferred embodiment particularly useful for achieving relatively high temperatures for long periods of time such as is required in sterilizations and in the cooking of, for example, meats.

FIG. 3 is a cross-sectional side elevation of another embodiment of the invention which is particularly advantageous for employment when the cooking or sterilization time must be of an exceptionally long time period. This device 310 differs essentially from the previous embodiments described in that the closed end 314 of the tubular containing 312 is divided on its interior by an integrally molded divider 315 into multiple recesses or open compartments 301 and 302, each of which is shown containing the heat-generating composition 354. In addition, separator 326 contains two funnel-like apertures 327 therethrough which are positioned over the recesses 301 and 302 respectively. Aligned over one of the funnels 327 is conduit 342 for carrying a charge of composition 354 or water to initiate the exothermic reaction of composition 354. As shown in FIG. 3, terminal end 343 of conduit 342 does not penetrate into the heat-generating zone 328 but provides the conduit passage required by cooperation with funnel 327. For purposes of clarity, the distance between terminal end 343 and separator 326 has been exaggerated. It is desirable that conduit 342 be of such length that the terminal end 343 is located just short of the surface of separator 326 so that there is a minimum communication between the heat-generating zone 328 and the heat-utilizing zone 332 via the funnel aperture 327. This assures that when added composition 354 is deposited in the conduit 342, steam pressure from below will not cause a dispersion of the falling composition 354 into the heat-utilizing chamber 332 by "Blowback".

In other respects, the device 310 is similar to the previously described embodiments in that it comprises a solid insulating wall 312 (shown here as a solid polymeric resin wall of low K factor), a clousre 318 of similar material held by a snapfit 320 over flange 322, vent 340, separator supporting projections 338, disposable liner 358, valve 346 to close conduit 342 and apertures 336 in separator 326 to permit the passage of gas and heat.

The device 310 of FIG. 3 is operated in the same manner as the previously described device 10 of FIG. 1, except that only one-half of the charge of composition 354 is initiated initially by adding water through conduit 342, i.e., into recess 302. When the chemical reaction of the charge in recess 302 terminates, the operator rotates closure 318 upon flange 322 so that conduit 342 is aligned with the funnel 327 over recess 301 and valve 342 is aligned with the funnel 327 over recess 301 and valve 342 is opened to permit the introduction of water into that portion of composition 354 which previously was substantially unreacted. [Some water will have condensed on the upper, inner walls 350 (or 358) and passed by gravity through the passage 360, reaching the edge or bottom of the composition 354 to initiate a minor reaction.]. Passage 360 is between separator 326 and the inside wall 350 of side wall 312. In this manner, the evolution of heat can be extended over a period of time nearly double that effected by a device such as device 10 described in FIG. 1. To aid in aligning the conduit 342 over the funnels 327, indicia can be printed or marked on the exterior of device 310 indicating their locations.

FIG. 4 is a cross-sectional view along lines 4—4 of FIG. 3 and shows in further detail the structural relationships of the separator 326 in the device 310.

Figure 5:
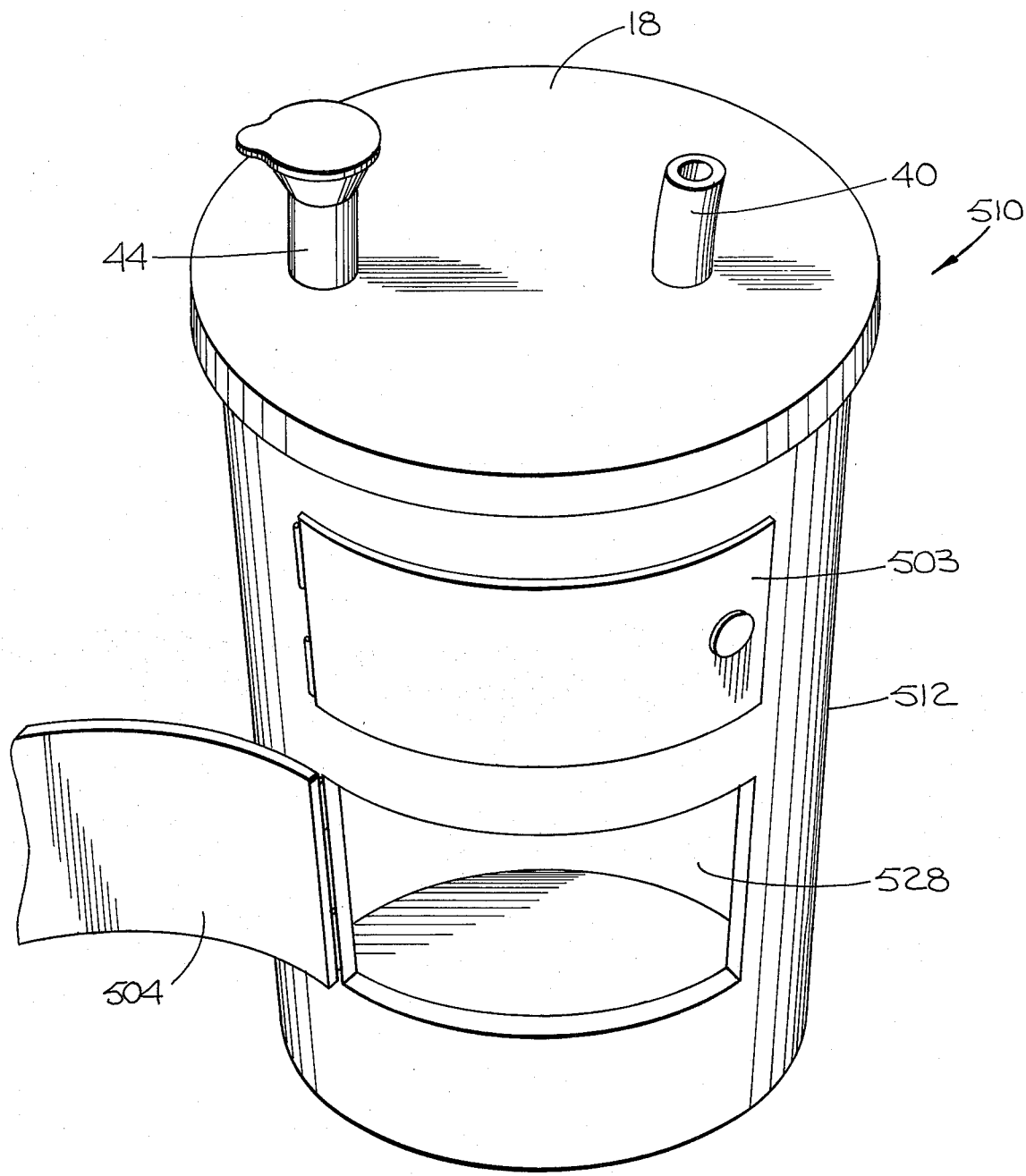
FIG. 5 is a view in perspective of an alternate embodiment of the invention.

FIG. 5 is a view in perspective of an alternate embodiment device of the invention 510 which differs essentially from the device 10 of FIG. 1 in that access means to the heat-generating 528 and heat-utilizing (not seen in FIG. 5) zones are provided for through the sidewall 512 by means of openings into the respective zones. The openings are closable by access doors 503 and 504, respectively, one being shown open and the other closed in FIG. 5. This embodiment provides an optional means of access to the interior of device 510. Further, for the purpose of commercial or institutional use the embodiment as shown in FIG. 5 (either upright or turned on its side 512) may be used in such a way so that one (or more) heat-generating (door entry type) zones can serve a multiplicity or cluster of heat-utilizing (door entry type) zones either stacked or in adjacent positions so that the heat which is released in the form of steam pressure may be transferred to the heat utilizing zones through one or more perforated wall openings, or piping, conduits or the like, so as to provide large scale caloric yields for use in such items as steam tables, push-carts and the like. Obviously more sophisticated means for automatic fueling and re-fueling and waste charge removal etc. could be employed without departing from the spirit of the invention.

Although the invention has been described above with reference to certain embodiments thereof for the purpose of simplicity in description, it should be understood that this invention is in no sense limited thereby and the scope of the invention is to be determined only by that of the appended claims. Many other variations of the invention will be obvious to those skilled in the art, for example, the devices of the invention may be provided wtih handles for lifting, wheels for portability and like variations which do not depart from the spirit of the invention.

I claim:

1. A unitary, self-contained apparatus for flameless heating which comprises;
    a tubular container having at least one closable opening;
    a closure for the opening;
    a chamber defined by said tubular container and closure;
    means for dividing the chamber into a heat-generating zone and a heat-utililzing zone, said means being pervious to heat and gases;
    means for venting said heat-utilizing zone to the exterior of said container; and
    a conduit communicating between the heat-generating zone of said chamber and the exterior of the closed container.

2. The apparatus of claim 1 wherein said tubular container is cylindrical.

3. The apparatus of claim 1 wherein said tubular container has one open end and one closed end.

4. The apparatus of claim 1 wherein said heat-utilizing zone is further divided into multiple heat-utilizing zones, by means pervious to gas and heat.

5. The apparatus of claim 1 wherein said vent is a pressure responsive valve adapted to open at a predetermined pressure differential between the interior and the exterior of said apparatus.

6. The apparatus of claim 1 wherein there is a means of opening and closing said conduit.

7. The apparatus of claim 1 wherein there is a passageway between the heat-generating zone and the heat-utilizing zone, located between the inner walls of said tubular container and the means for dividing the chamber.

8. The apparatus of claim 1 wherein said means of dividing is a perforated sheet.

9. The apparatus of claim 8 wherein said perforations are of a size to permit the passage of steam under pressure but insufficient to permit the ready passage of water.

10. The apparatus of claim 1 constructed of materials having a low thermal conductivity.

11. The apparatus of claim 1 including a disposable plastic liner for the interior thereof.

12. The apparatus of claim 1 wherein said tubular container is formed having double walls with a vacuum space in between.

13. The apparatus of claim 1 having openings in the sidewall thereof, fitted with closures.

14. The apparatus of claim 1 wherein the base of said heat-generating zone is divided into multiple open compartments.

* * * * *